United States Patent [19]
Breard

[11] Patent Number: 5,387,244
[45] Date of Patent: Feb. 7, 1995

[54] ARTIFICIAL HIP JOINT
[75] Inventor: Francis Breard, Paris, France
[73] Assignee: Science et Medecine (SEM), Montrouge, France
[21] Appl. No.: 23,205
[22] Filed: Feb. 25, 1993
[51] Int. Cl.⁶ ............................................. A61F 2/34
[52] U.S. Cl. .......................................... 623/23; 623/18
[58] Field of Search ....................... 623/16, 18, 22, 23

[56] References Cited
U.S. PATENT DOCUMENTS

| 4,141,088 | 2/1979 | Treace et al. | 623/22 |
| 4,172,296 | 10/1979 | D'Errico | 613/22 |
| 4,921,500 | 5/1990 | Averill et al. | 623/22 |
| 5,062,854 | 11/1991 | Noble et al. | 623/23 |

FOREIGN PATENT DOCUMENTS

| 0339530 | 11/1989 | European Pat. Off. | 623/23 |
| 0360734 | 3/1990 | European Pat. Off. | 623/23 |
| 0363019 | 4/1990 | European Pat. Off. | 623/23 |
| 2574283 | 6/1986 | France | 623/22 |
| 2652258 | 3/1991 | France | 623/22 |
| 2318396 | 10/1974 | Germany | 623/22 |

Primary Examiner—David Isabella
Attorney, Agent, or Firm—Collard & Roe

[57] ABSTRACT

An artificial hip joint between a femur and a pelvis having increased rotational clearance on an internal side of the joint, including an acetabular cup for anchoring to the pelvis. The hip joint includes a femoral prosthesis having an elongated stem for anchoring to the femur with an upper end. A collar extends outwardly from the upper end and terminates in an end part opposite the upper end of the stem. A head portion is supported on the end part and pivotally mounted within the acetabular cup. The head and the end part have a common central axis. The collar includes a surface on the internal side that contacts the acetabular cup. The surface is offset from the common central axis in a direction away from the internal side so that the acetabular cup has increased rotational clearance on the interior side.

18 Claims, 1 Drawing Sheet

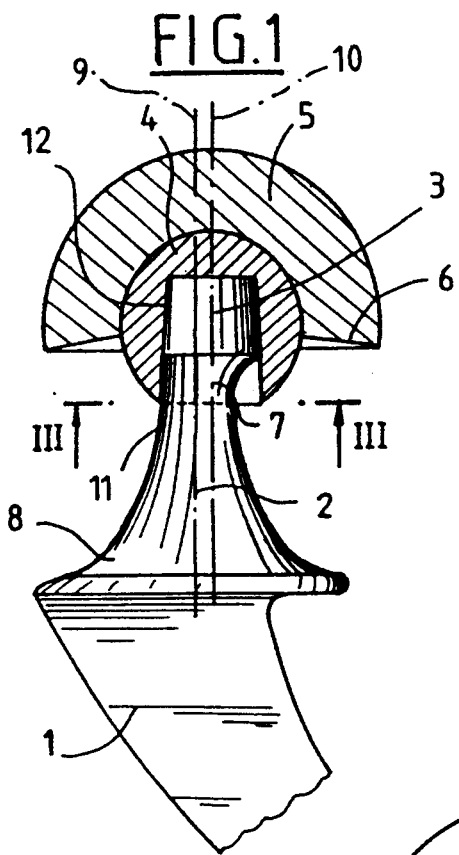
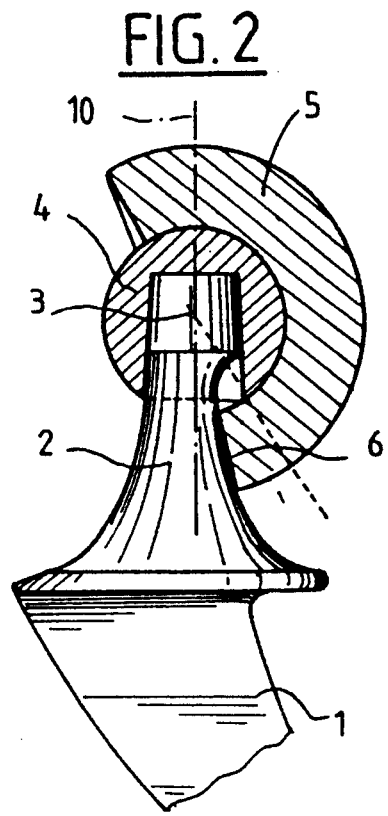
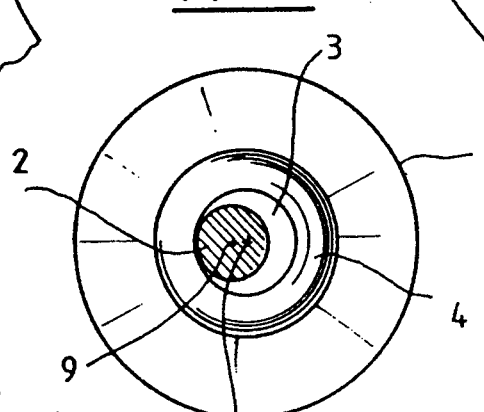
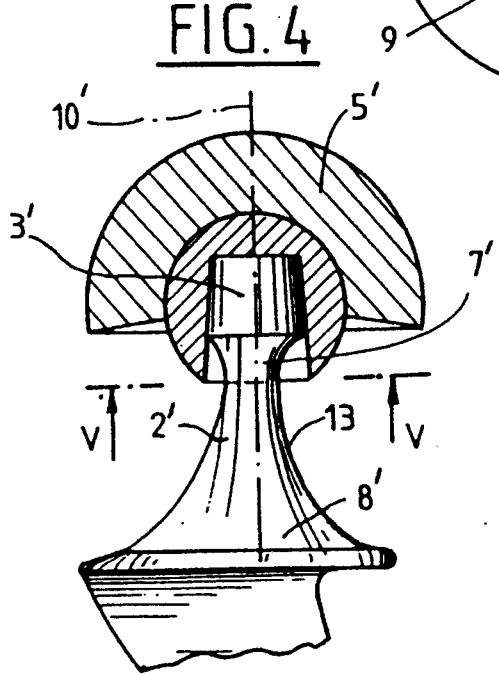
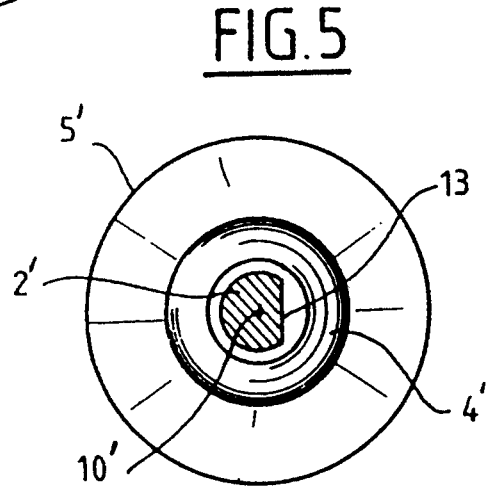

5,387,244

ARTIFICIAL HOP JOINT

BACKGROUND OF THE INVENTION

1. Field of the Invention

The present invention relates to an artificial hip joint having increased rotational clearance on the internal side of the joint. More specifically, it relates to a femoral prosthesis in which the collar is offset from the head portion.

2. The Prior Art

Artificial hip joints or prosthesis are known for replacing defective hip joints. The known hip prosthesis have a limitation in that the acetabular cup has limited clearance with respect to the collar of the femoral prosthesis. This can highly restrict the patient's movement if, for example, the patient were to assume a sitting position with one leg crossed over the other.

One attempt at solving the aforementioned drawback involved using rare metals, such as titanium, which has a sufficient strength to provide a collar with a reduced diameter. However, collars with reduced diameters less than 10 mm restrict the patient from walking which may cause the joint to luxate, i.e., dislocate.

SUMMARY OF THE INVENTION

It is an object of the present invention to overcome the drawbacks of the prior art and to provide an artificial hip joint which provides the patient with a greater range of motion.

It is yet another object of the present invention to provide an artificial hip joint which would allow the patient to walk without luxating.

These and other related objects are achieved according to the invention by an artificial hip joint between a femur and a pelvis having increased rotational clearance on an internal side of the joint and including an acetabular cup for anchoring to the pelvis. The hip joint includes a femoral prosthesis having an elongated stem for anchoring to the femur with an upper end, a collar extending outwardly from the upper end and terminates in an end part opposite the upper end of the stem. A head portion is supported on the end part and pivotally mounted within the acetabular cup. The head and the end part have a common central axis. The collar includes a surface on the internal side that contacts the acetabular cup. The surface is offset toward from the common central axis in a direction away from the internal side, so that the acetabular cup has increased rotational clearance on the internal side.

Although the offset of the collar limits rotational clearance in other planes, particularly the external side, the human anatomy only permits limited movement to the external side.

According to a preferred embodiment of the invention, the section of the collar between where it is connected to the upper end and the head portion, has rotational symmetry about its longitudinal, central axis. The central axis of the collar is offset from the common central axis of the head and end part in a direction away from the internal side. Since the collar has rotational symmetry across the majority of its length, it can be simply manufactured.

According to a further embodiment of the invention, the collar has rotational symmetry about its central axis and includes a plane surface on the internal side. The head, the end part and the collar have a common central axis. This embodiment may also be simply manufactured or may be utilized to redesign existing prosthesis. The end part of the collar is shaped as a truncated cone, and is contiguous with an exterior surface of the collar on the external side.

The acetabular cup includes a bevelled edge which contacts the plane surface of the collar in the maximum rotated position. In this manner, the contact surface between the acetabular cup and the collar is no longer a point but rather a line. This prevents wear and tear on the acetabular cup.

BRIEF DESCRIPTION OF THE DRAWINGS

Other objects and features of the present invention will become apparent from the following detailed description considered in connection with the accompanying drawings, which disclose two embodiments of the present invention. It should be understood, however, that the drawings are designed for the purpose of illustration only and not as a definition of the limits of the invention.

In the drawings, wherein similar reference characters denote similar elements throughout the several views:

FIG. 1 is a side elevational view, in part cross section, of the artificial hip joint according to the invention;

FIG. 2 is a side elevational view, in part cross section, with the acetabular cup in its maximum rotated position;

FIG. 3 is a cross-sectional view taken along the line III—III from FIG. 1;

FIG. 4 is a side-elevational view, in part cross section, of another embodiment of the artificial hip joint; and FIG. 5 is a cross-sectional view taken along the line V—V from FIG. 4.

DETAILED DESCRIPTION OF THE PREFERRED EMBODIMENTS

Referring now to the drawings and, in particular, FIGS. 1, 2 and 3, there is shown an artificial hip joint according to the invention made from metal, for example, titanium. The hip joint includes an elongated stem 1 for anchoring to the femur and having an upper end attached to a collar 2 which terminates in an end part 3 formed as a truncated cone. The larger end of the truncated cone faces stem 1. End part 3 is covered by a metallic head 4. An acetabular cup 5 is located in the pelvis and is configured and dimensioned to receive metallic head 4 and is generally made of plastic material. Acetabular cup 5 is hemispherically-shaped and limited on its lower end by a bevelled edge 6.

Collar 2 includes an upper connecting zone 7 connected to end part 3 and a lower connecting zone 8 connected to stem 1. The area between upper connecting zone 7 and lower connecting zone 8 has rotational symmetry about a central axis 9 of collar 2. End part 3 and head 4 have a common central axis 10. As can be seen in FIG. 3, axis 9 of collar 2 is displaced to the left or to the external side of axis 10.

As can be seen in FIG. 2, acetabular cup 5 is rotated to the internal side to the maximum rotated position. Bevelled edge 6 of acetabular cup 5 contacts collar 2 along a line rather than at a point. The leading bevelled edge 6 of the acetabular cup 5 was previously limited to the dotted line position. This dotted line represents the maximum rotational position of acetabular cup 5 intersecting with axis 10. Surprisingly, it was found that acetabular cup 5 can rotate up to an additional 10° beyond the dotted line, until it contacts collar 2. This additional 10° of rotation, affords the patient comfort and considerable safety while preventing any risk of the joint luxating.

An external surface 12 of end part 3 and an external surface 11 of collar 2 are aligned or contiguous with each other on the external side of the joint.

FIGS. 4 and 5 show an another embodiment of the hip joint in which end part 3' and collar 2' have a common central axis 10, as is typical with conventional prostheses. The middle region between upper connecting zone 7' and lower connecting zone 8' is formed as a plane surface 13 on the internal side of the collar. Existing prostheses can be provided with a plane surface 13 so as to provide an increased rotational clearance on the internal side of the joint. In the maximum rotated position, acetabular cup 5' contacts collar 2' along a surface not at a single point. Collar 2' can be simply manufactured since it has rotational symmetry along its length, with plane surface 13 being cut into the cylindrical collar 2'.

While only two embodiments of the present invention has been shown and described, it is to be understood that many changes and modifications may be made thereunto without departing from the spirit and scope of the invention as defined in the appended claims.

What is claimed is:

1. An artificial hip joint adapted for placement between a femur and a pelvis having a large rotational clearance on a medial side of the joint, comprising:
   an acetabular cup for anchoring to the pelvis;
   a femoral prosthesis having a proximal end and an elongated stem for anchoring to the femur; a neck extending outwardly from said proximal end and terminating in an end part opposite said proximal end of said stem; and a head portion configured to be supported on said end part and shaped to be pivotally mounted within said acetabular cup, said head and said end part having a common central axis, said neck including a surface on the medial side that is laterally offset toward said common central axis in a direction away from the medial side; and
   wherein said acetabular cup is rotatable in the medial direction to a maximum rotated position in which it contacts said laterally offset surface with said stem fully anchored in the femur.

2. An artificial hip joint adapted for placement between a femur and a pelvis with a large rotational clearance on a medial side of the joint, including an acetabular cup adapted for anchoring to the pelvis, comprising:
   (a) a femoral prosthesis having a proximal end and an elongated stem for anchoring to the femur;
   (b) a neck extending outwardly from said proximal end and terminating in an end part opposite said proximal end of said stem, wherein said neck includes;
      (i) an upper section adjacent to said end part;
      (ii) a lower section adjacent to said elongated stem and;
      (iii) a central region between said upper section and said lower section having a longitudinal axis, said central region having rotational symmetry about said longitudinal axis and including a planar surface formed on the medial side of the joint; and
   (c) a head portion configured to be supported on said end part and shaped to be pivotally mounted within the acetabular cup, said head and said end part having a common central axis; and
   (d) said planar surface being laterally offset toward said common central axis in a direction away from the medial side, so that the acetabular cup has a large rotational clearance on the medial side.

3. An artificial hip joint adapted for placement between a femur and a pelvis with a large rotational clearance on a medial side of the joint, including an acetabular cup adapted for anchoring to the pelvis, comprising:
   (a) a femoral prosthesis having a proximal end and an elongated stem for anchoring to the femur;
   (b) a neck extending outwardly from said proximal end and terminating in an end part opposite said proximal end of said stem;
   (c) a head portion configured to be supported on said end part and shaped to be pivotally mounted within the acetabular cup, said head and said end part having a common central axis;
   (d) said end part being disposed completely within said head; and
   (e) a contact surface on said neck, located at the periphery of said head on the medial side facing said head, and adapted for contacting the acetabular cup with said stem fully anchored in the femur, said contact surface is laterally offset toward said common central axis in a direction away from the medial side, so that the acetabular cup has a large rotational clearance on the medial side.

4. An artificial hip joint adapted for placement between a femur and a pelvis having a large rotational clearance on a medial side of the joint, comprising:
   (a) an acetabular cup for anchoring to the pelvis, said acetabular cup having an outer rim periphery with a bevelled edge;
   (b) a femoral prosthesis having an elongated stem for anchoring to the femur and including;
      (i) a proximal end;
      (ii) a neck extending outwardly from said proximal end and terminating in an end part opposite said proximal end, said end part being formed as a truncated cone having a first exterior surface, said neck having a second exterior surface contiguous to said first exterior surface, said cone having a first side with a diameter and a second spaced opposite side with a diameter smaller than said first side diameter, said first side facing said stem, said neck further including a contact surface located on a medial side of said neck adapted for contacting said acetabular cup, an upper section adjacent to said end part, a lower section adjacent to said elongated stem, and a central region between said upper section and said lower section having a longitudinal axis, said central region having rotational symmetry about said longitudinal axis;
   (c) a head portion configured to be supported on said end part and shaped to be pivotally mounted within said acetabular cup, said head and said end part having a common central axis;
   (d) said end part being disposed completely within said head; and
   (e) said longitudinal axis being offset from said common central axis in a direction away from said medial side;
   (f) wherein said contact surface is laterally offset toward said common central axis in a direction away from the medial side so that said acetabular cup is rotatable in the medial direction to a maximum rotated position wherein said bevelled edge contacts said contact surface with said stem fully anchored in the femur.

5. The device according to claim 3, wherein said neck includes an upper section adjacent to said end part and a lower section adjacent to said elongated stem and a central region between said upper section and said lower section having a longitudinal axis, said central region having rotational symmetry about said longitudinal axis, said longitudinal axis being offset from said common central axis in a direction away from said medial side.

6. The device according to claim 5, wherein said end part of said neck is formed as a truncated cone.

7. The device according to claim 6, wherein said truncated cone upper end includes a first side with a diameter and a second spaced opposite side with a diameter smaller than said first side diameter, said first side facing said stem.

8. The device according to claim 7, wherein said truncated cone end part has a first exterior surface and said neck has a second exterior surface contiguous to said first exterior surface.

9. The device according to claim 2, wherein said end part of said neck is formed as a truncated cone and is covered by said head portion.

10. The device according to claim 9, wherein said truncated cone upper end includes a first side with a first diameter and a second spaced opposite side with a second diameter smaller than said first diameter, said first side facing said stem.

11. The device according to claim 10, wherein said truncated cone end part has a first exterior surface and said neck has a second exterior surface contiguous to said first exterior surface.

12. The device according to claim 11 further comprising an acetabular cup rotatable in the medial direction to a maximum rotated position and having a bevelled edge which contacts said neck surface on said medial side of said neck in the maximum rotated position.

13. The device according to claim 12, wherein said femoral prosthesis is made from titanium.

14. The device according to claim 3, wherein said end part of said neck is formed as a truncated cone.

15. The device according to claim 6, wherein said truncated cone end part has a first exterior surface and said neck has a second exterior surface contiguous to said first exterior surface.

16. The device according to claim 1, wherein said end part of said neck is formed as a truncated cone; said truncated cone end part has a first exterior surface and said neck has a second exterior surface contiguous to said first exterior surface.

17. The device according to claim 2, further comprising an acetabular cup rotatable in the medial direction to a maximum rotated position and having an outer rim periphery With a bevelled edge which contacts said neck surface on said medial side of said neck in the maximum rotated position.

18. The device according to claim 3, further comprising an acetabular cup rotatable in the medial direction to a maximum rotated position and having an outer rim periphery with a bevelled edge which contacts said neck surface on said medial side of said neck in the maximum rotated position.

* * * * *